US009539192B2

(12) United States Patent
Odman Schmid et al.

(10) Patent No.: US 9,539,192 B2
(45) Date of Patent: Jan. 10, 2017

(54) HAIR COLOURING COMPOSITIONS, KITS, METHOD, AND USE THEREOF

(71) Applicant: NOXELL CORPORATION, Hunt Valley, MD (US)

(72) Inventors: Ozge Odman Schmid, Darmstadt (DE); Matija Crne, Wiesbaden (DE)

(73) Assignee: NOXELL CORPORATION, Hunt Valley, MD (US)

( * ) Notice: Subject to any disclaimer, the term of this patent is extended or adjusted under 35 U.S.C. 154(b) by 0 days.

(21) Appl. No.: 14/674,504

(22) Filed: Mar. 31, 2015

(65) Prior Publication Data

US 2015/0283053 A1 Oct. 8, 2015

(30) Foreign Application Priority Data

Apr. 2, 2014 (EP) ..................................... 14163250

(51) Int. Cl.
| | | |
|---|---|---|
| A61Q 5/10 | (2006.01) | |
| A61K 8/41 | (2006.01) | |
| A61K 8/92 | (2006.01) | |
| A61K 8/31 | (2006.01) | |
| A61K 8/34 | (2006.01) | |
| A61K 8/06 | (2006.01) | |

(52) U.S. Cl.
CPC ............... *A61K 8/411* (2013.01); *A61K 8/062* (2013.01); *A61K 8/064* (2013.01); *A61K 8/31* (2013.01); *A61K 8/342* (2013.01); *A61K 8/92* (2013.01); *A61Q 5/10* (2013.01); *A61K 2800/4324* (2013.01); *A61K 2800/882* (2013.01)

(58) Field of Classification Search
CPC ............ A61Q 5/10; A61K 8/22; A61K 8/062; A61K 8/064; A61K 8/92; A61K 2800/411; A61K 2800/4324
USPC .......................................................... 8/405
See application file for complete search history.

(56) References Cited

U.S. PATENT DOCUMENTS

| | | | |
|---|---|---|---|
| 2,273,564 A | 2/1942 | Dickey | |
| 2,528,378 A | 10/1950 | Mannheimer | |
| 2,781,354 A | 2/1957 | Mannheimer | |
| 4,976,742 A | 12/1990 | Rose | |
| 4,997,451 A | 3/1991 | Clausen | |
| 6,503,282 B1 | 1/2003 | Braun | |
| 6,648,923 B1 | 11/2003 | Goettel | |
| 7,591,860 B2 | 9/2009 | Sabelle | |
| 7,985,266 B2 | 7/2011 | Zhang | |
| 7,988,740 B2 | 8/2011 | Zhang | |
| 8,444,709 B2 | 5/2013 | Lim | |
| 8,444,710 B2 | 5/2013 | Lim | |
| 8,444,711 B2 | 5/2013 | Lim | |
| 8,444,712 B2 | 5/2013 | Lim | |
| 8,444,713 B2 | 5/2013 | Lim | |
| 8,444,714 B2 | 5/2013 | Lim | |
| 8,460,397 B2 | 6/2013 | Lim | |
| 2007/0107142 A1 | 5/2007 | Nguyen | |
| 2009/0119852 A1* | 5/2009 | Marsh ..................... | A61K 8/34 8/408 |
| 2010/0154141 A1* | 6/2010 | Hercouet ................. | A61K 8/06 8/416 |
| 2012/0012129 A1 | 1/2012 | Hagenow | |
| 2012/0078016 A1 | 3/2012 | Gardlik | |
| 2012/0130128 A1 | 5/2012 | Goettel | |
| 2012/0142969 A1 | 6/2012 | Gardlik | |
| 2012/0312318 A1 | 12/2012 | Krippahl | |
| 2013/0042882 A1 | 2/2013 | Goutsis | |
| 2013/0081647 A1 | 4/2013 | Vohra | |
| 2013/0340181 A1 | 12/2013 | Sutton | |

FOREIGN PATENT DOCUMENTS

| | | |
|---|---|---|
| CA | 2576189 A1 | 6/2007 |
| DE | 20107481 U1 | 7/2001 |
| DE | 102008061864 A1 | 10/2010 |
| EP | 1166749 B1 | 10/2005 |
| EP | 1765267 B1 | 1/2010 |
| FR | 2946648 A1 | 12/2010 |
| FR | 2945726 B1 | 6/2011 |
| FR | 2945731 B1 | 6/2011 |
| FR | 2945732 B1 | 6/2011 |
| FR | 2945734 B1 | 6/2011 |
| FR | 2945735 B1 | 6/2011 |
| FR | 2945736 B1 | 6/2011 |
| FR | 2945737 B1 | 6/2011 |
| FR | 2945740 B1 | 6/2011 |
| FR | 2945741 B1 | 6/2011 |
| FR | 2945744 B1 | 6/2011 |

(Continued)

OTHER PUBLICATIONS

Encyclopedia of Chemical Technology, Kirk-Othmer, Third Edition, 1982, vol. 3, pp. 896-900.
Encyclopedia of Chemical Technology, Kirk-Othmer, Third Edition, 1982, vol. 15, pp. 439-458.
Polymers in Nature by E. A. MacGregor and C. T. Greenwood, published by John Wiley & Sons, Chapter 6, pp. 240-328,1980.
Handbook of Surfactants by M. R. Porter, published by Blackie & Son (Glasgow and London), 1991, pp. 116-178.
Whistler, Roy L., Editor, "Industrial Gums—Polysaccharides and their Derivatives," Academic Press, Inc.

(Continued)

*Primary Examiner* — Eisa Elhilo
(74) *Attorney, Agent, or Firm* — Schwegman Lundberg & Woessner, P.A.

(57) ABSTRACT

The present invention relates to a hair coloring composition comprising in a cosmetically acceptable carrier one or more oxidizing agent(s), one or more alkalizing agent(s), one or more oxidative dye precursor(s) selected from the group consisting of 2-methoxymethyl-p-phenylenediamine, cosmetically acceptable salts thereof and mixtures thereof, one or more oil(s), wherein the composition comprises a total amount of oil(s) of more than 20%.

16 Claims, No Drawings

(56) References Cited

FOREIGN PATENT DOCUMENTS

| | | | |
|---|---|---|---|
| FR | 2946647 B1 | 6/2011 |
| FR | 2945738 B1 | 7/2011 |
| FR | 2945739 B1 | 7/2011 |
| FR | 2945756 B1 | 8/2011 |
| FR | 2945727 B1 | 8/2012 |
| FR | 2945733 B1 | 8/2012 |
| FR | 2945742 B1 | 8/2012 |
| FR | 2945743 B1 | 9/2012 |
| FR | 2945728 B1 | 10/2012 |
| FR | 2945729 B1 | 10/2012 |
| FR | 2945730 B1 | 10/2012 |
| WO | WO2010133573 A2 | 11/2010 |
| WO | WO2010133575 A2 | 11/2010 |
| WO | WO2010133639 A1 | 11/2010 |
| WO | WO2010133640 A2 | 11/2010 |
| WO | WO2010133803 A1 | 11/2010 |
| WO | WO2010133804 A2 | 11/2010 |
| WO | WO2010133805 A1 | 11/2010 |
| WO | WO2010139878 A2 | 12/2010 |
| WO | WO2010142776 A1 | 12/2010 |
| WO | WO2010142777 A1 | 12/2010 |

OTHER PUBLICATIONS

Goebel, Introduction of a methoxymethyl side chain into p-phenylenediamine attenuates its sensitizing potency and reduces the risk of allergy induction, Toxicology and Applied Pharmacology 274 (2014) pp. 480-487.

European Commission, Scientific Committee on Consumer Safety, 2-methoxy-methyl-p-phenylenediamine and its sulfate salt, Feb. 26, 2013.

* cited by examiner

HAIR COLOURING COMPOSITIONS, KITS, METHOD, AND USE THEREOF

FIELD OF THE INVENTION

The invention relates to a hair colouring composition comprising an oxidative dye precursor selected from the group consisting of 2-methoxymethyl-p-phenylenediamine, cosmetically acceptable salts thereof and mixtures thereof.

BACKGROUND OF THE INVENTION

The permanent alteration of the hair colour by the application of hair dyes is well known. In order to provide the consumer with the shade and the intensity of colour desired, a complex chemical process is utilized. Permanent hair dyeing formulations typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of colour. This reaction typically takes place at approximately pH 10 in the presence of an alkalizing agent and an oxidizing agent. Typically an oxidizing composition (also called developer and/or oxidizing component) comprising the oxidizing agent and a dye composition (also called tint or dye component) comprising the alkalizing agent and the precursors dye molecules are mixed shortly before use. The consumer repeats this process regularly in order to maintain the desired hair colour and shade and the intensity of colour and to ensure continual, even coverage of the hair including coverage of new hair growth.

Hair colouring formulations comprising one or more oxidative dye precursor(s) selected from the group consisting of 2-methoxymethyl-p-phenylenediamine, cosmetically acceptable salts thereof and mixtures thereof have been developed in the past. The inventors have noticed that when such hair colouring formulations are applied onto hair, they typically require a higher concentration of oxidative dye precursor(s) than formulations comprising other types of oxidative dye precursor(s) such as p-phenylene diamine or toluene-2,5-diamine to achieve a desired hair colour intensity. However, by increasing the concentration of oxidative dye precursor(s) comprised by these formulations, the end colour result along the entire length of hair (from roots to tips) coloured with such formulations may not always be homogeneous.

Therefore, there still exists a need for achieving a desired colour intensity of hair colored with these formulations without compromising the evenness of the overall end colour result.

The inventors have surprisingly found that by adding oil to a formulation comprising one or more oxidative dye precursor(s) selected from the group consisting of 2-methoxymethyl-p-phenylenediamine, cosmetically acceptable salts thereof and mixtures thereof, it is possible to reduce the concentration of oxidative dye precursor(s) comprised by these formulations in order to achieve a desired hair colour intensity. Consequently, a more even overall end colour result may be obtained.

SUMMARY OF THE INVENTION

The present invention relates to a hair colouring composition comprising, in cosmetically acceptable carrier:

one or more oxidizing agent(s);
one or more alkalizing agent(s);
one or more oxidative dye precursor(s) selected from the group consisting of 2-methoxymethyl-p-phenylenediamine, cosmetically acceptable salts thereof and mixtures thereof;
one or more oil(s),
wherein the composition comprises a total amount of oil(s) of more than 20%, or at least 30%, or at least 50% by total weight of the composition.

The present invention also relates to a hair colouring composition comprising a first component and a second component wherein:
a) the first component comprises, in a cosmetically acceptable carrier:
    one or more alkalizing agent(s);
    one or more oxidative dye precursor(s) selected from the group consisting of 2-methoxymethyl-p-phenylenediamine, cosmetically acceptable salts thereof and mixtures thereof;
b) the second component comprises, in a cosmetically acceptable carrier one or more oxidizing agent(s) and
wherein at least one of the first and second components comprises one or more oil(s) and the total amount of oil(s) in the composition after mixing the first component and the second component is of more than 20%, or at least 30%, or at least 50% by total weight of the composition.

Furthermore, the present invention also relates to a kit for colouring hair and to a method for colouring hair with such compositions.

Finally, the present invention also relates to the use of one or more oil(s) for increasing the colour intensity of hair which are colored with a composition comprising one or more oxidizing agent(s), one or more alkalizing agent(s) and one or more oxidative dye precursor(s) selected from the group consisting of 2-methoxymethyl-p-phenylenediamine, cosmetically acceptable salts thereof and mixtures thereof.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

By "hair colouring" composition it is meant a composition suitable for changing the colour of hair. The hair colouring composition is referred hereinafter as "the composition", unless otherwise specified.

All percentages are by weight of the total hair coloring composition, i.e. of the ready-to-use composition, unless otherwise specified. When more than one composition are used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

"oil" is used herein to refer to an organic compound insoluble in water at normal temperature (25° C.) and at atmospheric pressure (760 mmHg), i.e. it has a water solubility of less than 5% by weight, or less than 1% by weight, or less than 0.1% by weight. Oils have in their structure a chain of at least two siloxane groups or at least one hydrocarbon chain having at least 6 carbon atoms. Furthermore, oils are generally soluble in organic solvents in the same conditions of temperature and pressure, for example in chloroform, ethanol, benzene or decamethylcyclopentasiloxane. Furthermore, oils are liquid at ordinary temperature (25° C.) and at atmospheric pressure (760 mmHg). The oils preferably do not contain any carboxylic acid functions, i.e. they do not contain any —COOH or —COO⁻ groups.

Hair Colouring Composition

The present invention relates to a hair colouring composition comprising, in a cosmetically acceptable carrier: one or more oxidizing agent(s), one or more alkalizing agent(s), one or more oxidative dye precursor(s) selected from the group consisting of 2-methoxymethyl-p-phenylenediamine, cosmetically acceptable salts thereof and mixtures thereof and one or more oil(s). The composition comprises a total amount of oil(s) of more than 20% by total weight of the composition.

Emulsions

The present invention also relates to a hair colouring composition comprising a first component (A) and a second component (B). The first component (A) comprises, in a cosmetically acceptable carrier one or more alkalizing agent(s) and one or more oxidative dye precursor(s) selected from the group consisting of 2-methoxymethyl-p-phenylenediamine, cosmetically acceptable salts thereof and mixtures thereof. The second component (B) comprises, in a cosmetically acceptable carrier one or more oxidizing agent(s). At least one of the first and second components (A) and (B) comprises one or more oil(s).

The total amount of oil(s) in the composition after mixing the first component (A) and the second component (B) is of more than 20% by total weight of the composition.

The first and the second components (A) and (B) may be mixed at a ratio of from 5:1 to 1:5, or from 3:1 to 1:3, or from 2:1 to 1:2, or of 1:1.

The first component (A) may be an oil-in-water direct emulsion comprising a total amount of oil(s) ranging from 5% to 40%, or from 10% to 30% by total weight of the first component (A) and the second component (B) may be a water-in-oil inverse emulsion comprising a total amount of oil(s) ranging from 20% to 70% by total weight of the second component (B).

Alternatively, the first component (A) may be a water-in-oil inverse emulsion comprising a total amount of oil(s) ranging from 30% to 70%, or from 40% to 65% by total weight of the first component (A) and the second component (B) may be a water-in-oil inverse emulsion comprising a total amount of oil(s) ranging from 30% to 70% by total weight of the second component (B).

The second component (B) may comprise a total amount of oil(s) ranging from 30% to 65%, or from 40% to 65% by total weight of the second component (B).

The inverse emulsions (water-in-oil) and direct emulsions (oil-in-water) according to the present invention are true emulsions, and should be distinguished from microemulsions, which are thermodynamically stable systems, unlike true emulsions.

The emulsions may be prepared via standard processes for preparing inverse or direct emulsions, which are well known to those skilled in the art. The size of the droplets of the dispersed phase of the inverse or direct emulsions may be from 10 nm to 100 μm or from 200 nm to 50 μm.

The term "size of the droplets of the dispersed phase" is used herein to refer to the mean diameter D(3.2) of the droplets, which may be measured especially using a laser granulometer.

The hair colouring compositions according to the present invention are particularly advantageous. Indeed, by introducing oil(s) into hair colouring compositions comprising 2-methoxymethyl-p-phenylenediamine it is possible to increase the colour intensity of hair which are coloured with such compositions. Therefore, a reduced concentration of 2-methoxymethyl-p-phenylenediamine comprised by these compositions can be used in order to achieved a desired colour intensity. By reducing the concentration of 2-methoxymethyl-p-phenylenediamine a more homogeneous end colour result along the entire length of hair may therefore be obtained.

Oil(s)

The composition comprises one or more oil(s). As mentioned hereinbefore, the composition comprises a total amount of oil(s) of more than 20% by total weight of the composition. The composition may comprise a total amount of oil(s) of at least 30% or at least 50% by total weight of the composition.

Alternatively, the composition may comprise a total amount of oil(s) ranging from 25% to 70%, or from 30% to 70%, or from 40% to 70% or from 50% to 70% by total weight of the composition.

The oil(s) may be selected from the group consisting of lower alkanes, fatty alcohols, esters of fatty acid, esters of fatty alcohol, non-silicone oils of animal, vegetable, mineral or synthetic origin, non-silicone waxes, silicones and mixtures thereof.

The fatty alcohols and esters may have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

When the composition of the invention is obtained by mixing a developer component and a dye component, the oil(s) may be incorporated into the developer component and/or the dye component. Alternatively, the oil(s) may be incorporated into a separate component, i.e. an oil component which is mixed with the developer component and the dye component.

Lower Alkanes

"Lower alkanes" is used herein to refer to alkanes having from 6 to 16 carbon atoms and being linear or branched or cyclic. Lower alkanes may be selected from the group consisting of hexane, dodecane, isoparaffins such as isohexadecane and isodecane and mixtures thereof.

Fatty Alcohols

The fatty alcohols may be selected from non-alkoxylated, saturated or unsaturated, linear or branched alcohols having from 6 to 30 carbon atoms and more particularly from 8 to carbon atoms. The fatty alcohols may be selected from cetyl alcohol, stearyl alcohol and their mixture (cetylstearyl alcohol), octyldodecanol, 2-butyloctanol, 2-hexyldecanol, 2-undecylpentadecanol, oleic alcohol, linoleic alcohol and mixtures thereof.

Fatty Esters

The esters of fatty acid or of fatty alcohol may be the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisononate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The esters may be $C_6$-$C_{30}$ or $C_{12}$-$C_{22}$ fatty acid esters and diesters of sugar. "Sugar" is used herein to refer to oxygen-containing hydrocarbon compounds that comprise several alcohol functions, with or without aldehyde or ketone functions, and that comprise at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, especially alkyl derivatives, such as methyl derivatives, for example methylglucose.

The esters of sugars and of fatty acids may, for example, be chosen from the esters or mixtures of esters of sugars described previously and of linear or branched, saturated or unsaturated $C_6$-$C_{30}$ or $C_{12}$-$C_{22}$ fatty acids. If they are unsaturated, these compounds can have one to three, conjugated or unconjugated, carbon-carbon double bonds.

The esters may also be selected from mono-, di-, tri- and tetra-esters, polyesters and mixtures thereof.

The esters may be selected from oleates, laurates, palmitates, myristates, behenates, cocoates, stearates, linoleates, linolenates, caprates, arachidonates, or mixtures thereof such as oleo-palmitate, oleo-stearate, palmito-stearate mixed esters.

Non-limiting mention can be made of the product sold under the name Glucate® DO by the company Amerchol, which is a methylglucose dioleate.

Non-Silicone Oils of Animal, Vegetable, Mineral or Synthetic Origin

The non-silicone oils may be selected from hydrocarbon oils of animal origin, such as perhydrosqualene.

The non-silicone oils may be selected from hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Steanineries Dubois or those sold under the names Miglyol® 810, 812 and 818 by the company Dynamit Nobel, jojoba oil, shea butter oil.

The non-silicone oils may be selected from hydrocarbons with more than 16 carbon atoms, linear or branched, of mineral or synthetic origin, such as paraffin oils, petroleum jelly, liquid paraffin, polydecenes, hydrogenated polyisobutene such as Parleam®.

Non-Silicone Waxes

The non-silicone waxes may be selected from carnauba wax, candelilla wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (Cera Bettina); other waxes or waxy raw materials usable according to the disclosure are, for example, marine waxes such as that sold by the company SOPHIM under reference M82, waxes of polyethylene or of polyolefins in general.

Silicones

The silicones usable in the composition according to the present invention include but are not limited to volatile or non-volatile, cyclic, linear or branched silicones, modified or not with organic groups, having a viscosity from $5 \times 10^{-6}$ to 2.5 m²/s at 25° C., or from $1 \times 10^{-5}$ to 1 m²/s.

The silicones may be in the form of oils, waxes, resins or gums.

The silicones may be selected from polydialkylsiloxanes, such as the polydimethylsiloxanes (PDMS), and organo-modified polysiloxanes having at least one functional group selected from poly(alkoxylated) groups, amine groups and alkoxy groups. The organopolysiloxanes are defined in more detail in the work of Walter NOLL "Chemistry and Technology of Silicones" (1968), Academic Press. They can be volatile or non-volatile.

When they are volatile, the silicones may, for example, be selected from those with a boiling point between 60° C. and 260° C., and for further examples, selected from cyclic polydialkylsiloxanes having from 3 to 7 or from 4 to 5 silicon atoms. It can be, for example, the octamethylcyclotetrasiloxane marketed under the name Volatile Silicone® 7207 by Union Carbide or Silbione® 70045 V2 by Rhodia, the decamethylcyclopentasiloxane marketed under the name Volatile Silicone® 7158 by Union Carbide or Silbione® 70045 V5 by Rhodia, and mixtures thereof. Non-limiting mentions can also be made of the cyclocopolymers of the dimethylsiloxanes/methylalkylsiloxane type, such as Volatile Silicone® FZ 3109 by Union Carbide, of formula:

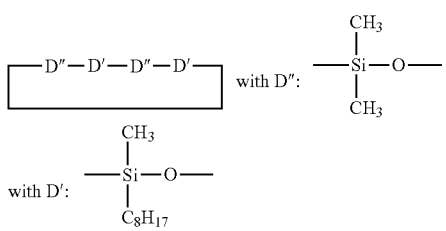

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bis-neopentane.

Other suitable volatile silicones include the linear volatile polydialkylsiloxanes having 2 to 9 silicon atoms and with a viscosity of less than or equal to $5 \times 10^{-6}$ m$^2$/s at 25° C. An example is decamethyltetrasiloxane, marketed under the name "SH 200" by the company TORAY SILICONE. Silicones included in this class are also described in the article published in Cosmetics and Toiletries, Vol. 91, January 76, p. 27-32—TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from polydialkylsiloxanes, such as polydimethylsiloxanes with trimethylsilyl end groups. The viscosity of the silicones is measured at 25° C. according to Standard Test Method for Kinematic Viscosity of Transparent and Opaque Liquids (and Calculation of Dynamic Viscosity).

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the poly-isobutylenes, methylene chloride, pentane, dodecane, tridecane and mixtures thereof.

The organopolysiloxane resins usable according to the disclosure include but are not limited to crosslinked siloxane systems containing the units: $R_2SiO_{2/2}$, $R_3SiO_{1/2}$, $RSiO_{3/2}$ and $SiO_{4/2}$ wherein R represents an alkyl having 1 to 16 carbon atoms. For example, R denotes a $C_1$-$C_4$ lower alkyl group such as methyl.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1 \times 10^{-5}$ to $5 \times 10^{2}$ m$^2$/s at 25° C.

The oil(s) may not comprise any oxyalkylene units or any glycerol units.

The oil(s) preferably do not contain any carboxylic acid functions, i.e. they do not contain any —COOH or —COO$^-$ groups. In case the oil(s) contain a carboxylic acid function, the oil(s) may for example be oleic acid.

The oil(s) may be selected from liquid paraffin, liquid petroleum jelly, polydecenes, liquid esters of fatty acid, liquid esters of fatty alcohol, liquid fatty alcohols, and mixtures thereof, alternatively from liquid petroleum jelly, polydecenes, liquid fatty alcohols and mixtures thereof, alternatively from liquid paraffin, liquid petroleum jelly and mixtures thereof.

The amount of each particular oil or mixtures thereof described hereinbefore can account for up to 100% (or 100%) of the total amount of oil(s) in the composition.

Oxidizing Agent(s)

The composition comprises one or more oxidizing agent(s). Any oxidizing agent known in the art may be used. Preferred oxidizing agents are water-soluble peroxygen oxidizing agents. As used herein, "water-soluble" means that in standard conditions at least about 0.1 g, preferably about 1 g, more preferably about 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

The composition may comprise a total amount of oxidizing agent(s) ranging from 0.1% to 10%, alternatively from 1% to 7%, alternatively from 2% to 5%, by total weight of the composition. The amount of each particular oxidizing agent or mixtures thereof described hereinafter can account for up to 100% (or 100%) of the total amount of oxidizing agent(s) in the composition.

Suitable water-soluble oxidizing agents include, but are not limited to: inorganic peroxygen materials capable of yielding hydrogen peroxide in an aqueous solution. Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agent(s) can be used if desired. The oxidizing agent(s) may be provided in aqueous solution or as a powder which is dissolved prior to use.

The composition may comprise one or more water-soluble oxidizing agent(s) selected from the group consisting of hydrogen peroxide, percarbonates, persulphates, and mixtures thereof.

A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Preferred sources of carbonate ions, carbamate and hydrocarbonate ions are sodium hydrogen carbonate, potassium hydrogen carbonate, ammonium carbamate, and mixtures thereof.

When the composition of the present invention is obtained by mixing a developer component and a dye component prior to use, the oxidizing agent(s) may be present in the developer component. The developer component may be based on any desired formulation chassis, including any commercial product. Typical developer components comprise about 6% or about 9% of the $H_2O_2$ relative to the total weight of the developer composition. A commercial example is the Welloxon® Emulsion with respectively about 6% and about 9% $H_2O_2$, marketed by Wella and comprising as INCI ingredients: Water, $H_2O_2$, Cetearyl Alcohol, Ceteareth-25, Salicylic Acid, Phosphoric Acid, Disodium Phosphate, Etidronic Acid.

Alkalizing Agent(s)

The composition comprises one or more alkalizing agent(s). Any alkalizing agent(s) known in the art may be used. Typically, the composition may comprise a total amount of alkalizing agents ranging from 0.1% to 10%, alternatively from 0.5% to 6%, alternatively from 1% to 4%, by total weight of the composition. The amount of each particular alkalizing agent or mixtures thereof described hereinafter can account for up to 100% (or 100%) of the total amount of alkalizing agent(s) in the composition.

The alkalizing agent(s) may be selected from the group consisting of ammonia, ammonium hydroxide, ammonium carbonate, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates and mixtures thereof. Alternatively, the alkalizing agent (s) may be selected from the group consisting of ammonia, ammonium hydroxide, monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof. Alternatively, the alkalizing agent may be monoethanolamine.

Preferably, if present, the ammonium ions and carbonate ions are present in the composition at a weight ratio of from 3:1 to 1:10, alternatively from 2:1 to 1:5.

When the composition of the present invention is obtained by mixing a developer component and a dye component prior to use, the alkalizing agent(s) is/are generally present in the dye component.

The composition may be substantially free of ammonia. The term "substantially free of ammonia" means that the composition of the present invention is either completely free of ammonia (including ammonium ions) or contains no appreciable amount of ammonia (including ammonium ions), for example, no more than 1%, or no more than 0.5%, or no more than 0.3%, or no more than 0.1%, by total weight of the composition. In the embodiments wherein the composition is substantially free of ammonia, the composition may comprise an alkanolamine such as monoethanolamine.

Oxidative Dye Precursors

The composition comprises one or more oxidative dye precursor(s) selected from the group consisting of 2-methoxymethyl-p-phenylenediamine, cosmetically acceptable salts thereof and mixtures thereof. The salts of 2-methoxymethyl-p-phenylenediamine may be selected from sulphate salt, chloride salt, oxalate salt and mixtures thereof.

The composition may comprise a total amount of oxidative dye precursor(s) selected from the group consisting of 2-methoxymethyl-p-phenylenediamine, cosmetically acceptable salts thereof and mixtures thereof ranging from 0.01% to 2%, alternatively from 0.5% to 2.00 by total weight of the composition.

The composition may further comprise additional oxidative dye precursors which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the composition may comprise a total amount of oxidative dye precursor(s) ranging up to 12%, alternatively from 0.1% to 10%, alternatively from 0.3% to 8%, alternatively from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1 (5H)-one dimethosulfonate, 4,5-diamino-1-hexylpyrazole, 4,5-diamino-1-heptylpyrazole, N,N-bis(2-hydroxyethyl)-N-(4-aminophenyl)-1,2-diaminothane, salts thereof and mixtures thereof. Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl) diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the composition of the invention is obtained by mixing a developer component and a dye component, the primary intermediates and couplers are usually incorporated into the dye component.

Cosmetically Acceptable Carrier

The composition comprises a cosmetically acceptable carrier. The cosmetically acceptable carrier may be selected from water, or a mixture of water and at least one organic solvent to dissolve the compounds that would not typically be sufficiently soluble in water.

Suitable organic solvents include, but are not limited to: $C_1$ to $C_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The cosmetically acceptable carrier may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount of less than 70%, or less than 50% or less than 30%, by total weight of the composition. Typically, when present, the composition comprises a total amount of organic solvents ranging from 1% to 30%, by total weight of the composition.

Other Ingredients

The composition according to the present invention may comprise, in addition to the ingredients indicated above, further ingredients in order to further enhance the properties of the composition, as long as these are not excluded by the claims.

Suitable further ingredients include, but not limited to: direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Direct Dyes

The composition may further comprise compatible direct dyes, in an amount sufficient to provide additional coloring, particularly with regard to intensity. Typically, the composition may comprise a total amount of direct dyes ranging from 0.05% to 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the composition is obtained by mixing a dye component and a developer component, the direct dyes are usually incorporated into the dye component.

Chelants

The composition may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference. Typically, the composition may comprise a total amount of chelants ranging from at least 0.01%, alternatively from 0.01% to 5%, alternatively from 0.25% to 3%, alternatively from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

The composition may comprises a chelant selected from the group consisting of diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof. Alternatively, the composition may comprise ethylenediaminedisuccinic acid (EDDS) as a chelant.

When the composition of the invention is obtained by mixing a tint component and a developer component, the chelants may be incorporated in the tint component and/or in the developer component. A chelant is usually present in the developer component for stability reason.

Radical Scavengers

The composition may further comprise one or more radical scavenger(s). As used herein the term "radical scavenger" refers to a species that can react with a radical, e.g. a carbonate radical, to convert the radical by a series of fast reactions to a less reactive, or un-reactive species. The radical scavenger may be different from the alkalising agent and/or is present in an amount sufficient to reduce the damage to the hair during the colouring process.

The composition may comprise a total amount of radical scavenger(s) ranging from 0.1% to 10%, alternatively from 1% by weight to 7%, by total weight of the composition. Suitable radical scavengers include, but are not limited to: alkanolamines, amino sugars, amino acids, esters of amino acids, pyrazolones, such as those discussed in US 2011/0035885A1 and US 2011/0035886A1, and mixtures thereof; alternatively monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof, 3-carboxy-1H-pyrazol-5-one, 3-carboxy-1-phenyl-pyrazol-5-one, 3-carboxy-1-(4-sulfophenyl)-pyrazol-5-one, 3-carboxy-1-(4-carboxyphenyl)-pyrazol-5-one, and mixtures thereof; alternatively glycine, sarcosine, lysine, serine, 2-methoxyethylamine, glucosamine, glutamic acid, morpholine, piperidine, ethylamine, 3-amino-1-propanol, and mixtures thereof.

pH Modifiers and Buffering Agents

The composition may further comprise, in addition to the alkalizing agent(s) discussed above, a pH modifier and/or buffering agent in an amount that is sufficiently effective to adjust the pH of the composition to fall within a range from 3 to 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulants (such as inorganic and inorganic acids including for example phosphoric acid, acetic acid, ascorbic acid, citric acid or tartaric acid, hydrochloric acid); and mixtures thereof.

Thickeners and/or Rheology Modifiers

The composition may further comprise one or more thickener(s) in an amount sufficient to provide the composition with a viscosity so that it can be readily applied to the hair without unduly dripping off the hair and causing mess.

The composition may comprise a total amount of thickener(s) ranging from at least 0.1%, alternatively at least 0.5%, alternatively at least 1%, by total weight of the composition. Suitable thickeners include, but are not limited to: associative polymers, polysaccharides, non-associative polycarboxylic polymers, and mixtures thereof.

Carbonate Ion Sources

The composition may further comprise a source of carbonate ions, carbamate ions, hydrogen carbonate ions, and mixtures thereof in a sufficient amount to reduce damage to the hair during the coloring process.

The composition may comprise a total amount of a carbonate ion source ranging from 0.1% to 15%, alternatively from 0.1% to 10%, alternatively from 1% to 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The composition may further comprise one or more conditioning agent(s), and/or be used in combination with a composition comprising one or more conditioning agent(s).

The composition may comprise a total amount of conditioning agent(s) ranging from 0.05% to 20%, alternatively from 0.1% to 15%, alternatively from 0.2% to 10%, alternatively from 0.2% to 2%, alternatively from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Surfactants

The composition may further comprise one or more surfactant(s). The composition may comprise a total amount of surfactant(s) ranging from 1% to 60%, alternatively from 2% to 30%, alternatively from 8% to 25%, alternatively from 10% to 20%, by total weight of the composition. The composition may comprise a total amount of anionic surfactants ranging from 0.1% to 20%, alternatively from 0.1% to 15%, alternatively from 5% to 15%, by total weight of the composition; and a total amount of amphoteric and/or nonionic surfactants, which may range independently from each other from 0.1% to 15%, alternatively from 0.5% to 10%, alternatively from 1% to 8%, by total weight of the composition.

In the embodiments wherein the composition comprises a first component (A) and a second component (B) wherein the first component (A) is an oil-in-water direct emulsion or a water-in-oil inverse emulsion and the second component (B) is a water-in-oil inverse emulsion, the first component (A) and the second component (B) comprise one or more surfactants. In these embodiments, the surfactants may be selected from the group consisting of anionic surfactants, cationic surfactants, amphoteric surfactants, nonionic surfactants and mixtures thereof, alternatively from the group consisting of nonionic surfactants and/or anionic surfactants, alternatively from nonionic surfactants.

The anionic surfactants may be selected from the salts (in particular alkali metal salts, especially sodium salts, ammonium salts, amino salts such as amino alcohol salts or alkaline-earth metal salts such as magnesium salts) of the following compounds:
  alkyl sulfates, alkyl ether sulfates, alkylamido ether sulfates, alkylaryl polyether sulfates, monoglyceride sulfates;
  alkylsulfonates, alkylamidesulfonates, alkylarylsulfonates, a-olefin sulfonates, paraffin sulfonates;
  alkyl phosphates, alkyl ether phosphates;
  alkylsulfosuccinates, alkyl ether sulfosuccinates, alkylamidesulfosuccinates;
  alkylsulfosuccinates;
  alkylsulfo acetates;
  acylsarcosinates; acylisethionates and N-acyltaurates;
  salts of fatty acids such as oleic acid, ricinoleic acid, palmitic acid or stearic acid, coconut oil acid or hydrogenated coconut oil acid;
  alkyl-D-galactoside uronic acid salts;
  acyllactylates;
  salts of polyoxyalkylenated alkyl ether carboxylic acids, of polyoxyalkylenated alkylaryl ether carboxylic acids or of polyoxyalkylenated alkylamido ether carboxylic acids, in particular those containing from 2 to 50 ethylene oxide groups;
  and mixtures thereof.

It should be noted that the alkyl or acyl radical of these various compounds advantageously comprises from 6 to 24 or from 8 to 24 carbon atoms, and the aryl radical advantageously comprises a phenyl or benzyl group.

The nonionic surfactants may be selected from oxyalkylenated or glycerolated nonionic surfactants.

Oxyalkylenated Nonionic Surfactants

The oxyalkylenated nonionic surfactants may be monooxyalkylenated or polyoxyalkylenated nonionic surfactants.

The oxyalkylene units may be oxyethylene units and/or oxypropylene units.

Examples of oxyalkylenated nonionic surfactants that may be mentioned include:
  oxyalkylenated ($C_8$-$C_{24}$)alkylphenols,
  saturated or unsaturated, linear or branched, oxyalkylenated $C_8$-$C_{30}$ alcohols,
  saturated or unsaturated, linear or branched, oxyalkylenated $C_8$-$C_{30}$ amides,
  esters of saturated or unsaturated, linear or branched, $C_8$-$C_{30}$ acids and of polyethylene glycols,
  polyoxyethylenated esters of saturated or unsaturated, linear or branched, $C_8$-$C_{30}$ acids and of sorbitol,
  saturated or unsaturated, oxyethylenated plant oils,
  condensates of ethylene oxide and/or of propylene oxide,
  and mixtures thereof.

These surfactants contain a number of moles of ethylene oxide and/or of propylene oxide ranging from 1 to 100 of from 2 and 50.

Advantageously, the nonionic surfactants do not comprise any oxypropylene units.

The oxyalkylenated nonionic surfactants may be selected from oxyethylenated $C_8$-$C_{30}$ alcohols, and esters of $C_8$-$C_{30}$ acids and of polyethylene glycols.

Glycerolated Nonionic Surfactants

The glycerolated nonionic surfactants may be monoglycerolated or polyglycerolated nonionic surfactants. The glycerolated nonionic surfactants may be monoglycerolated or polyglycerolated $C_8$-$C_{40}$ alcohols.

In particular, the monoglycerolated or polyglycerolated $C_8$-$C_{30}$ alcohols may correspond to the following formula:

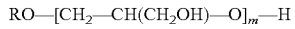

$$RO\text{---}[CH_2\text{---}CH(CH_2OH)\text{---}O]_m\text{---}H$$

in which R represents a linear or branched $C_8$-$C_{40}$ or $C_8$-$C_{30}$ alkyl or alkenyl radical, and m represents a number ranging from 1 to 30 or from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it may be advantageous to use the $C_8$-$C_{10}$ alcohols containing 1 mol of glycerol, the $C_{10}$-$C_{12}$ alcohol containing 1 mol of glycerol and the $C_{12}$ alcohol containing 1.5 mol of glycerol.

As mentioned hereinbefore, the first component (A) and the second component (B) may comprise one or more nonionic surfactant(s). The first component (A) may comprise one or more nonionic surfactant(s) with an HLB value of greater than or equal to 8 and/or the second component (B) may comprise one or more nonionic surfactant(s) with an HLB value of less than 8.

The first component (A) and/or the second component (B) may comprise a total amount of surfactant(s) ranging from 1% to 20%, or from 1% to 15%, or from 2% to 10% by total weight of respectively the component (A) or (B).

Ionic Strength

The composition may further have an ionic strength as defined hereinafter of less than 1.35 mole/kg, alternatively from 0.10 to 0.75 mole/kg, alternatively from 0.20 to 0.60 mole/kg. Whilst not being bound by theory, it is believed that the ionic strength value may also affect the resultant viscosity and root adhesion properties of the composition.

The ionic strength can be affected by salt resources such as the dyes, sodium sulphate, ammonium carbonate anti-oxidants and chelants such as EDDS. In some embodiments, dyes used as salts may have the greatest effect on the ionic strength and thus the amounts added in order to provide any particular shade need to be considered in terms of ionic strength as well as dye outcome in order to prevent viscosity and root adhesion problems.

The ionic strength of the composition is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength. For example the ionic strength of a mixed 0.050 M $Na_2SO_4$ and 0.020 M NaCl solution is: I=½((2×(+1)²×0.050)+(+1)²×0.020+(−2)²×0.050+(−1)²×0.020)=0.17 M.

Viscosity

The composition may have a viscosity of from 1000 to 60000 cPs, alternatively from 2000 to 30000 cPs, alternatively from 3000 to 25000 cPs. Viscosity is measured using Brookfield viscometers with cone and plate attachment. For viscosities in the range of 0 to 12000 cPs, the Brookfield DV-11 viscometer with S42 plate is used. 2 ml sample of the composition is equilibrated at 26.7° C. for three minutes before the readings are taken at 1 rpm. For viscosities in the range of 12,000 to 60,000 cPs, the Brookfield DV-1 viscometer with S52 plate is used. 0.5 ml sample of the composition is equilibrated for 1 minute at 26.7° C. before the readings are taken at 1 rpm.

Foam

The composition may be provided in the form of foam which is applied to the hair. Foam formation is typically achieved by the use of a foaming agent incorporated within the mixed composition (typically present in either the developer component or the dye component or both) in combination with a manually operated foaming device. Such manually operated foaming devices are known in the art and include aerosols devices, squeeze foamers and pump foamers.

Suitable foaming agents include surfactants such as anionic, nonionic and amphoteric surfactants, particularly nonionic surfactants; polysaccharides; polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Hair Colouring Kit

In another aspect of the present invention, the present invention relates to a kit for colouring hair. The kit may be either a 2-part kit or a 3-part kit.

2—Part Kit

The kit may comprise a first and a second unit comprising respectively the first component (A) and the second component (B) as defined hereinbefore. The first and the second units may be separated containers or they may be two compartments within a same container.

The consumer mixes the first component (A) and the second component (B) together immediately before use and applies it onto the hair or apply successively and without intermediate rinsing the first component (A) and the second component (B) onto hair.

For the professional hair salon market, the first component (A) and the second component (B) are typically supplied independently to allow the professional to select a preferred combination.

3—Part Kit

The kit may comprise a first, a second and a third unit. The first unit may comprise a first composition comprising one or more alkalizing agent(s) and one or more oxidative dye precursor(s) selected from the group consisting of 2-methoxymethyl-p-phenylenediamine, cosmetically acceptable salts thereof and mixtures thereof. The second unit may comprise a second composition comprising one or more oxidizing agent(s). The third unit may comprise a third composition comprising one or more oil(s). The oil(s) may be selected from any oil(s) which have been described hereinbefore. The first, second and third units may be separated containers or they may be three compartments within a same container.

For the professional hair salon market, the first, second and third compositions are typically supplied independently to allow the professional to select a preferred combination. The consumer mixes the first and the second units of the 2-part kit or the first, the second and the third units of the 3-part kit together immediately before use and applies it onto the hair.

After working the combined mixture for a few minutes (to ensure uniform application to all of the hair), the hair colouring composition is allowed to remain on the hair for an amount sufficient for the dyeing to take place (usually from 2 to 60 minutes, typically 30 to 45 minutes). The consumer or salon professional then rinses the hair thoroughly with water and/or shampoo and allows it to dry. It will be observed that the hair has changed from its original colour to the desired colour.

The 2-part kit or the 3-part kit may also comprise respectively a third or a fourth unit comprising a component selected from the group consisting of a conditioning composition, a pre-treatment composition, a colour refresher composition, a dilutant composition.

The pre-treatment composition may be applied onto hair, before applying the hair colouring composition.

The conditioning composition, comprising a conditioning agent, may be mixed together with the first and the second components (A) and (B) prior to application onto hair, or may be alternatively applied onto hair, for example after applying the hair colouring composition.

The colour refresher composition comprising optionally a pre-formed dye, may be applied to the hair after applying the hair colouring composition, e.g. from 1 minute after to 60 days after applying the hair colouring composition. The colour refresher composition can be used to increase the initial colour obtained and/or boost the colour during the wash and style cycle until the next oxidative hair colouring event.

The dilutant composition may comprise water and optionally at least one active component. The dilutant composition may for example be the dilutant component which is disclosed in WO 2013/126657 A2.

Hair Colouring Method

In another aspect of the present invention, the present invention relates to a method of colouring hair.

The method may comprise the steps of: providing a first composition comprising one or more alkalizing agent(s) and one or more oxidative dye precursor(s) selected from the group consisting of 2-methoxymethyl-p-phenylenediamine, cosmetically acceptable salts thereof and mixtures thereof; providing a second composition comprising one or more alkalizing agent(s); providing a third composition comprising one or more oil(s): mixing the first, second and third compositions for obtaining a hair colouring composition; applying the obtained composition onto hair; optionally leaving the applied composition on hair for a sufficient amount of time, e.g. from 2 min to 60 min, alternatively 10 min to 40 min; optionally rinsing hair using a rinsing composition or water; optionally cleansing hair using a cleansing composition; optionally treating hair with a conditioning and/or treating composition; and, optionally drying hair.

Alternatively, the method may comprise the steps of: providing a first component (A) as defined hereinbefore; providing a second component (B) as defined hereinbefore; mixing the first component (A) and the second component (B) for obtaining a hair colouring composition and applying the obtained composition onto hair or applying successively and without intermediate rinsing the first component (A) and the second component (B) onto hair; optionally leaving the applied composition on hair for a sufficient amount of time, e.g. from 2 min to 60 min, alternatively 10 min to 40 min; optionally rinsing hair using a rinsing composition or water; optionally cleansing hair using a cleansing composition; optionally treating hair with a conditioning and/or treating composition; and, optionally drying hair.

Use

In another aspect of the present invention, the present invention relates to the use of one or more oil(s) for increasing the colour intensity of hair which are colored with a hair colouring composition comprising one or more oxidizing agent(s), one or more alkalizing agent(s) and one or more oxidative dye precursor(s) selected from the group consisting of 2-methoxymethyl-p-phenylenediamine, cosmetically acceptable salts thereof and mixtures thereof.

There are a number of industry-accepted ways to measure the increase of color intensity in this context. The CIE L C h colour system is used as a standard method of measuring colour (ref: Industrial Colour Testing, p 20, by Hans G. Volz, ISBN 3-527-30436-3). Using this method it is possible to assess the improvement in optical properties of hair fibres by monitoring the L and C values using for example a handheld spectrophotometer such as Minolta 3600d or Ocean Optics USB 2000+, which is based on diffuser measurement geometry.

Packaging and Dispensing Devices

The present invention may be provided in a variety of packaging devices and/or dispensing devices. These dispensing devices can come in the form of separate devices which may be used independently or in combination with one another. Typically, the hair colouring compositions are contained within separate single or multi compartment containers so that the compositions can be stored separately from one another before use. The compositions are then mixed together by a mixing means and then dispensed from the device and applied to the consumer's hair by an application means.

In the embodiments, wherein the hair colouring composition comprises a first component (A) and a second component (B) as defined hereinbefore, the most common packaging device which can be used for the present invention involves storing the second component (B), i.e. the developer component, in a container such as a bottle, tube, aerosol, or a sachet and separately storing the first component (A), i.e. the dye component, in an additional compartment within the developer container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the developer component and the dye component by any means. This may simply involve the use of a mixing bowl into which the compositions are dispensed and then mixed, preferably using a mixing means such as a tool. Alternatively, it may involve the addition of one of the components into the container of the other component (typically the dye component is added to the developer component), followed by manual shaking or mixing with a tool. Another system involves the perforation or displacement of a seal located between the separate compartments of the dye component and developer component within a single container or sachet followed by manual mixing within the container or in a separate and or additional container.

The devices described herein above can also be used in combination with a product delivery and or application tool to aid application of the product onto the hair, including using a nozzle attached to one of the containers, using a separate applicator device such as a comb or brush, using a comb attached to or instead of the dispensing nozzle whereby the product is dispensed through hollow tines and dispensing apertures located in the comb tines. The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used. Additional device technology can be used to assist in the penetration of the product into the hair. Examples of such technology include heating devices, ultraviolet light devices and ultrasound devices.

The hair colouring composition, and the corresponding first and second components (A) and (B) as defined hereinfore, may be manufactured by conventional processes known in the art for manufacturing oxidative hair colouring and/or bleaching products, and ad-mixing the ingredients of each component composition in suitable vessels, followed by packaging in appropriate individual containers.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

Example 1

The following dye component is prepared. The dye component A1 is in the form of a oil-in-water direct emulsion.

| Dye component (A1) | Weight % |
| --- | --- |
| Ascorbic acid | 0.25 |
| 2-Methoxymethyl-p-Phenylenediamine | 0.21 |
| 1-Hydroxy-4-aminobenzene | 0.2 |
| Resorcinol | 0.1 |
| 1-Methyl-2-hydroxy-4-p-hydroxyethylaminobenzene | 0.25 |
| 1-Methyl-2-hydroxy-4-aminobenzene | 0.28 |
| Liquid paraffin | 20 |
| C16/C18 cetylstearyl alcohol (30/70) | 8 |
| Cetylstearyl alcohol 33 OE | 3 |
| Sodium stannate hexahydrate | 0.04 |
| Oxyethylenated rapeseed acid amide (4 OE) | 1.5 |
| Vitamin E | 0.1 |
| Glycerol | 1 |
| Monoethanolamine | 4 |
| Water | qs 100 |

The following developer component is prepared. The developer component B1 is in the form of a water-in-oil inverse emulsion.

| Developer component (B1) | Weight % |
| --- | --- |
| Liquid petroleum jelly | 51.5 |
| Octyldodecanol | 9 |
| Distearyldimethylammonium-modified hectorite | 1.3 |
| Propylene carbonate | 0.45 |
| Oleth-3 | 6 |
| Propylene glycol | 2 |
| Ethanol | 3 |
| Hexylene glycol | 1 |
| Dipropylene glycol | 1 |
| POE/POP/POE (Poloxamer 184) | 13 |
| Hydrogen peroxide | 6 |
| Sodium stannate hexahydrate | 0.04 |
| Diethylenetriaminepentaacetic acid | 0.015 |
| Tetrasodium pyrophosphate decahydrate | 0.03 |
| Phosphoric acid | qs pH = 3 |
| Water | qs 100 |

The dye component is mixed with the developer component at a mixing ratio of 1:1. The resulting mixture is then applied to swatches of natural hair containing at least 90% white hairs. After a leave-on time of 30 min at room temperature (23° C.), the hair is rinsed, washed with a standard shampoo and then dried.

Example 2

The following dye component is prepared. The dye component A2 is in the form of a water-in-oil inverse emulsion.

| Dye component (A2) | Weight % |
| --- | --- |
| Liquid petroleum jelly | 51.5 |
| Octyldodecanol | 9 |
| Distearyldimethylammonium-modified hectorite | 1.3 |
| Propylene carbonate | 0.45 |
| Oleth-10 | 4.3 |
| Propylene glycol | 2 |
| Ethanol | 3 |
| Hexylene glycol | 1 |
| Dipropylene glycol | 1 |
| Monoethanolamine | 4 |
| POE/POP/POE (Poloxamer 184) | 13 |
| Ascorbic acid | 0.25 |
| 2-Methoxymethyl-p-Phenylenediamine | 0.042 |
| Resorcinol | 0.04 |
| 1-Hydroxy-3-aminobenzene | 0.002 |

| Dye component (A2) | Weight % |
| --- | --- |
| 1-P-Hydroxyethyloxy-2,4-diaminobenzene dihydrochloride | 0.0003 |
| N,N-Bis(2-hydroxyethyl)-p-phenylenediamine sulfate monohydrate | 0.006 |
| Water | qs 100 |

The following developer component is prepared. The developer component B2 is in the form of a water-in-oil inverse emulsion.

| Developer component (B2) | Weight % |
| --- | --- |
| Liquid paraffin | 40 |
| PEG-30 dipolyhydroxystearate (Arlacel P135) | 4 |
| Isosorbide laurate (Arlamol ISML) | 1 |
| Ammonium acryloyldimethyltaurate/steareth-25 methacrylate crosslinked copolymer | 2 |
| Magnesium sulfate | 0.3 |
| Hydrogen peroxide | 6 |
| Sodium stannate hexahydrate | 0.04 |
| Diethylenetriam inepentaacetic acid | 0.015 |
| Tetrasodium pyrophosphate decahydrate | 0.03 |
| Phosphoric acid | qs pH = 3 |
| Water | qs 100 |

The dye component is mixed with the developer component at a mixing ratio of 1:1. The resulting mixture is then applied to swatches of natural hair containing at least 90% white hairs. After a leave-on time of 30 min at room temperature (23° C.), the hair is rinsed, washed with a standard shampoo and then dried.

Experimental Data:

| Ingredients | Composition C (Weight %) | Composition D (Weight %) |
| --- | --- | --- |
| Cetearyl Alcohol (and) Sodium Lauryl Sulfate | 7.66 | 7.66 |
| Glyceryl Stearate SE | 2.41 | 2.41 |
| Lanolin Alcohol | 0.875 | 0.875 |
| Glycol Distearate | 0.875 | 0.875 |
| Sodium Laureth Sulfate | 1.75 | 1.75 |
| Sodium sulfite | 0.175 | 0.175 |
| Sodium Cocoyl Isethionate | 0.201 | 0.201 |
| EDTA disodium salt | 0.0438 | 0.0438 |
| Ascorbic acid | 0.131 | 0.131 |
| 2-Methoxymethyl-p-Phenylenediamine | 0.394 | 0.394 |
| Resorcinol | 0.241 | 0.241 |
| m-Aminophenol | 0.0241 | 0.0241 |
| 2-Methylresorcinol | 0.0241 | 0.0241 |
| Monoethanolamine | 3.06 | 3.06 |
| Hydrogen Peroxide Solution, 50% | 3.13 | 3.13 |
| Liquid paraffin [1] | 50 | 0 |
| Water | qs 100 | qs 100 |

[1] Marcol 82 from Exxon Mobil

The above hair colouring compositions C and D have been prepared. Composition C is a composition according to the present invention, i.e. it comprises 2-methoxymethyl-p-phenylenediamine and oil (liquid paraffin) whereas composition D is the same composition as composition C but does not comprise oil. Each of the compositions is applied to a different swatch of natural hair containing at least 90% white hairs. After a leave-on time of 30 min at 30° C., the hair was rinsed, washed with a standard shampoo conditioned with a standard conditioner and then dried. The L value (lightness value) of the hair swatches coloured with each of the hair colouring composition C or D was measured using an Ocean Optics USB 2000+ spectrophotometer.

The measured L value (lightness value) is reported in the following table:

| Sample | L |
| --- | --- |
| Composition C | 22.1 |
| Composition D | 28.9 |

As can be seen in the table, the L value measured for the composition C according to the present invention is lower than the L value measured for the composition D. This shows that the colour intensity of hair colored with composition C is higher than the colour intensity of hair coloured with composition D. These data demonstrates that by introducing oil(s) into a hair colouring composition comprising 2-methoxymethyl-p-phenylenediamine, it is possible to increase the intensity of hair coloured with such a composition. Therefore, by introducing oil(s) into such a composition it is possible to reduce the concentration of 2-methoxymethyl-p-phenylenediamine which is comprised in this composition in order to achieve a desired colour intensity. Consequently, a more homogeneous end colour result along the entire length of hair may be observed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related Patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colouring composition comprising, in a cosmetically acceptable carrier:
   one or more oxidizing agent(s);
   one or more alkalizing agent(s);
   one or more oxidative dye precursor(s) selected from the group consisting of 2-methoxymethyl-p-phenylenediamine, cosmetically acceptable salts thereof and mixtures thereof;
   liquid paraffin oil,
   wherein the composition comprises a total amount of oil(s) of more than 20% by total weight of the composition.

2. The hair colouring composition according to claim 1, wherein the composition comprises a total amount of liquid paraffin oil of at least 30% by total weight of the composition.

3. The hair colouring composition according to claim 1, wherein the composition comprises a total amount of liquid paraffin oil of at least 50% by total weight of the composition.

4. The hair colouring composition according to claim 1, wherein the alkalizing agent(s) is selected from the group consisting of ammonia, ammonium hydroxide, ammonium carbonate, alkanolamines, guanidium salts, alkali metal hydroxides, alkali metal carbonates and mixtures thereof.

5. The hair colouring composition according to claim 1, wherein the alkalizing agent(s) is selected from the group consisting of ammonia, ammonium hydroxide, monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof.

6. A hair colouring composition comprising a first component (A) and a second component (B) wherein:
   a) the first component (A) comprises, in a cosmetically acceptable carrier:
      one or more alkalizing agent(s);
      one or more oxidative dye precursor(s) selected from the group consisting of 2-methoxymethyl-p-phenylenediamine, cosmetically acceptable salts thereof and mixtures thereof;
   b) the second component (B) comprises, in a cosmetically acceptable carrier one or more oxidizing agent(s) and
   wherein at least one of the first and second components (A) and (B) comprises liquid paraffin oil and the total amount of liquid paraffin oil in the composition after mixing the first component (A) and the second component (B) is of more than 20% by total weight of the composition.

7. The hair colouring composition according to claim 6, wherein the total amount of liquid paraffin oil in the composition after mixing the first component (A) and the second component (B) is of at least 30% by total weight of the composition.

8. The hair colouring composition according to claim 6, wherein the total amount of liquid paraffin oil in the composition after mixing the first component (A) and the second component (B) is of at least 50% by total weight of the composition.

9. The hair colouring composition according to claim 6, wherein the first and the second components (A) and (B) are mixed in a ratio of from about 5:1 to about 1:5.

10. The hair colouring composition according to claim 6, wherein the first component (A) is an oil-in-water direct emulsion comprising a total amount of oil(s) ranging from about 5% to about 40% by total weight of the first component (A) and the second component (B) is a water-in-oil inverse emulsion comprising a total amount of liquid paraffin oil ranging from about 20% to about 70% by total weight of the second component (B).

11. The hair colouring composition according to claim 6, wherein the first component (A) is a water-in-oil inverse emulsion comprising a total amount of oil(s) ranging from about 30% to about 70% by total weight of the first component (A) and the second component (B) is a water-in-oil inverse emulsion comprising a total amount of liquid paraffin oil ranging from about 30% to about 70% by total weight of the second component (B).

12. The hair colouring composition according to claim 6, wherein the second component (B) comprises a total amount of liquid paraffin oil ranging from about 30% to about 65%, by total weight of the second component (B).

13. The hair colouring composition according to claim 6, wherein the first component (A) and/or the second component (B) comprise one or more surfactant(s).

14. The hair colouring composition according to claim 6, wherein the alkalizing agent(s) is selected from the group consisting of ammonia, ammonium hydroxide, ammonium carbonate, alkanolamines, guanidium salts, alkali metal hydroxides, alkali metal carbonates and mixtures thereof.

15. The hair colouring composition according to claim 6, wherein the alkalizing agent(s) is selected from the group consisting of ammonia, ammonium hydroxide, monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof.

16. A method for colouring hair comprising applying onto hair a composition comprising, in a cosmetically acceptable carrier:
- one or more oxidizing agent(s);
- one or more alkalizing agent(s);
- one or more oxidative dye precursor(s) selected from the group consisting of 2-methoxymethyl-p-phenylenediamine, cosmetically acceptable salts thereof and mixtures thereof;
- liquid paraffin oil,
- wherein the composition comprises a total amount of oil(s) of more than 20% by total weight of the composition.

* * * * *

UNITED STATES PATENT AND TRADEMARK OFFICE
CERTIFICATE OF CORRECTION

PATENT NO. : 9,539,192 B2  
APPLICATION NO. : 14/674504  
DATED : January 10, 2017  
INVENTOR(S) : Odman Schmid et al.

Page 1 of 1

It is certified that error appears in the above-identified patent and that said Letters Patent is hereby corrected as shown below:

On the Title Page

Item (30), in "Foreign Application Priority Data", in Column 1, Line 1, delete "14163250" and insert --14163250.5-- therefor Item (57), in "Abstract", in Column 2, Line 1, delete "coloring" and insert --colouring-- therefor Signed and Sealed this  
Third Day of April, 2018

Andrei Iancu  
*Director of the United States Patent and Trademark Office*